(12) United States Patent
Robinson et al.

(10) Patent No.: US 7,690,264 B2
(45) Date of Patent: Apr. 6, 2010

(54) METHOD AND APPARATUS FOR APPLYING BENDING LOAD TO AN AXLE OF AN AIRCRAFT LANDING GEAR

(75) Inventors: Guy Robinson, Bristol (GB); Fraser F L Wilson, Bristol (GB)

(73) Assignee: Airbus Operations Limited, Bristol (GB)

( * ) Notice: Subject to any disclaimer, the term of this patent is extended or adjusted under 35 U.S.C. 154(b) by 10 days.

(21) Appl. No.: 11/797,271

(22) Filed: May 2, 2007

(65) Prior Publication Data

US 2007/0256504 A1 Nov. 8, 2007

(30) Foreign Application Priority Data

May 8, 2006 (GB) ................... 0609049.2

(51) Int. Cl.
*G01N 3/32* (2006.01)
(52) U.S. Cl. ........................................ 73/812
(58) Field of Classification Search ............. 73/812
See application file for complete search history.

(56) References Cited

U.S. PATENT DOCUMENTS

| 3,713,330 | A | * | 1/1973 | Lentz | 73/115.07 |
|---|---|---|---|---|---|
| 4,133,201 | A | * | 1/1979 | Klinger | 73/12.01 |
| 4,501,139 | A | * | 2/1985 | Petersen | 73/117.01 |
| 4,658,656 | A | * | 4/1987 | Haeg | 73/669 |
| 4,761,991 | A | * | 8/1988 | Fembock | 73/11.07 |
| 4,862,738 | A | * | 9/1989 | Jankowski | 73/115.07 |
| 4,863,266 | A | * | 9/1989 | Masuko et al. | 356/139.09 |
| 4,951,504 | A | * | 8/1990 | Klock et al. | 73/117.03 |
| 5,487,301 | A | * | 1/1996 | Muller et al. | 73/117.03 |
| 5,569,836 | A | * | 10/1996 | Hill | 73/11.07 |
| 5,942,673 | A | * | 8/1999 | Horiuchi et al. | 73/11.04 |
| 6,035,715 | A | * | 3/2000 | Porter | 73/571 |
| 6,247,366 | B1 | * | 6/2001 | Porter | 73/571 |
| 7,146,859 | B2 | * | 12/2006 | Dittmann et al. | 73/669 |
| 7,369,966 | B1 | * | 5/2008 | Scelsi et al. | 702/185 |
| 7,401,520 | B2 | * | 7/2008 | Parison | 73/669 |
| 2007/0257150 | A1 | * | 11/2007 | Robinson et al. | 244/103 R |

FOREIGN PATENT DOCUMENTS

RU 1076816 2/2004
SU 583389 12/1977

* cited by examiner

*Primary Examiner*—Lisa M Caputo
*Assistant Examiner*—Freddie Kirkland, III
(74) *Attorney, Agent, or Firm*—Nixon & Vanderhye P.C.

(57) ABSTRACT

Apparatus for applying bending load to an axle of an aircraft landing gear. The apparatus comprises a dummy wheel having a dummy wheel bearing; and a load tool having a convex outer surface which is configured to engage the dummy wheel when in use so as to bend the axle via the dummy wheel bearing. The dummy wheel is shaped to enable it to roll over the convex outer surface of the load tool as the axle bends. The load tool has a load tool bearing which permits the load tool to move as it bends the axle. One or more sensors are provided to sense the load applied to the axle; and one or more sensors are provided to sense the response of the axle to the applied load.

21 Claims, 6 Drawing Sheets

METHOD AND APPARATUS FOR APPLYING BENDING LOAD TO AN AXLE OF AN AIRCRAFT LANDING GEAR

FIELD OF THE INVENTION

The present invention relates to a method and apparatus for applying bending load to an axle of an aircraft landing gear.

BACKGROUND OF THE INVENTION

In a conventional aircraft landing gear, a wheel is fitted to an axle via a wheel bearing. It is desirable to test the performance of the landing gear by simulating the bending load applied to the axle by the wheel bearing. In order to accurately quantify the performance of the landing gear it is desirable to apply a precisely known load to the axle at a precisely known position.

SUMMARY OF THE INVENTION

A first aspect of the invention provides apparatus for applying bending load to an axle of an aircraft landing gear, the apparatus comprising a dummy wheel with a dummy wheel bearing; and a load tool having a convex outer surface which is configured to engage the dummy wheel when in use so as to applying bending load to the axle via the dummy wheel bearing, wherein the dummy wheel is shaped to enable it to roll over the convex outer surface of the load tool as the axle bends.

A second aspect of the invention provides a method of applying bending load to an axle of an aircraft landing gear, the method comprising: fitting a dummy wheel to the axle via a dummy wheel bearing; and applying the bending load to the axle by engaging the dummy wheel with a convex outer surface of a load tool, wherein the bending of the axle causes the dummy wheel to roll over the convex outer surface of the load tool.

In order to be suitable for testing a landing gear of a relatively large aircraft, the dummy wheel is typically rated to support a bending load greater than 100 KN. However it will be appreciated that the apparatus may also be used to test the landing gear of a relatively small aircraft, in which bending loads as low as 1 KN may be applied.

The rolling motion between the dummy wheel and the load tool gives low frictional losses compared with a sliding arrangement. These low frictional losses enable a precisely known load to be applied to the dummy wheel. Also, the convex shape of the outer surface of the load tool provides a small area of contact with the dummy wheel. This enables the load tool to apply load to the dummy wheel at a precisely known position.

The rolling motion may be provided by a jewel bearing, or in a preferred embodiment by a load tool which engages the dummy wheel directly.

Typically the load tool has a load tool bearing which permits the load tool to move as it applied the bending load. This enables the load tool to apply the load to the dummy wheel at a position which does not vary (or only varies slightly) as the axle bends. The load tool bearing may be a rotary bearing which permits the load tool to rotate as it applies the load to the axle. However preferably the load tool bearing is a linear load tool bearing which permits the load tool to move in a straight line as it applies the load to the axle. This prevents the load tool from inducing unwanted load components as it moves.

The load tool bearing may be a fluid bearing provided by a layer of oil film, or a rolling-element bearing.

The load tool bearing may permit the load tool to move only in a single direction, but more preferably permits the load tool to move in two orthogonal directions. This may be achieved for example by a two-dimensional film of oil, or a two-dimensional array of ball-bearings.

The dummy wheel may have a generally flat surface, or a slightly curved concave surface. Preferably the dummy wheel is formed with a series of recesses formed in its surface, the recesses being sized to receive the convex outer surface of the load tool. This enables the load tool to be accurately positioned in a series of indexed positions relative to the axle. In a preferred embodiment the recesses are formed in a generally flat surface. Each recess may have a locally planar surface (for instance the recess may be V-shaped in cross-section) but preferably each recess has a curved concave surface with a relatively high radius of curvature compared with the radius of curvature of the convex outer surface of the load tool. Preferably each recess (and optionally the convex outer load surface of the load tool) is elongate in shape when viewed in plan.

An actuator (such as a hydraulic cylinder) may be provided to apply bending load to the axle in a different direction to the load tool. Typically the actuator is connected to the dummy wheel at one end and to another axle of the aircraft landing gear at another end.

Typically one or more sensors (such as strain gauges) are provided for sensing the load applied to the axle; and one or more sensors (such as strain gauges) are provided for sensing the response of the axle to the applied load.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
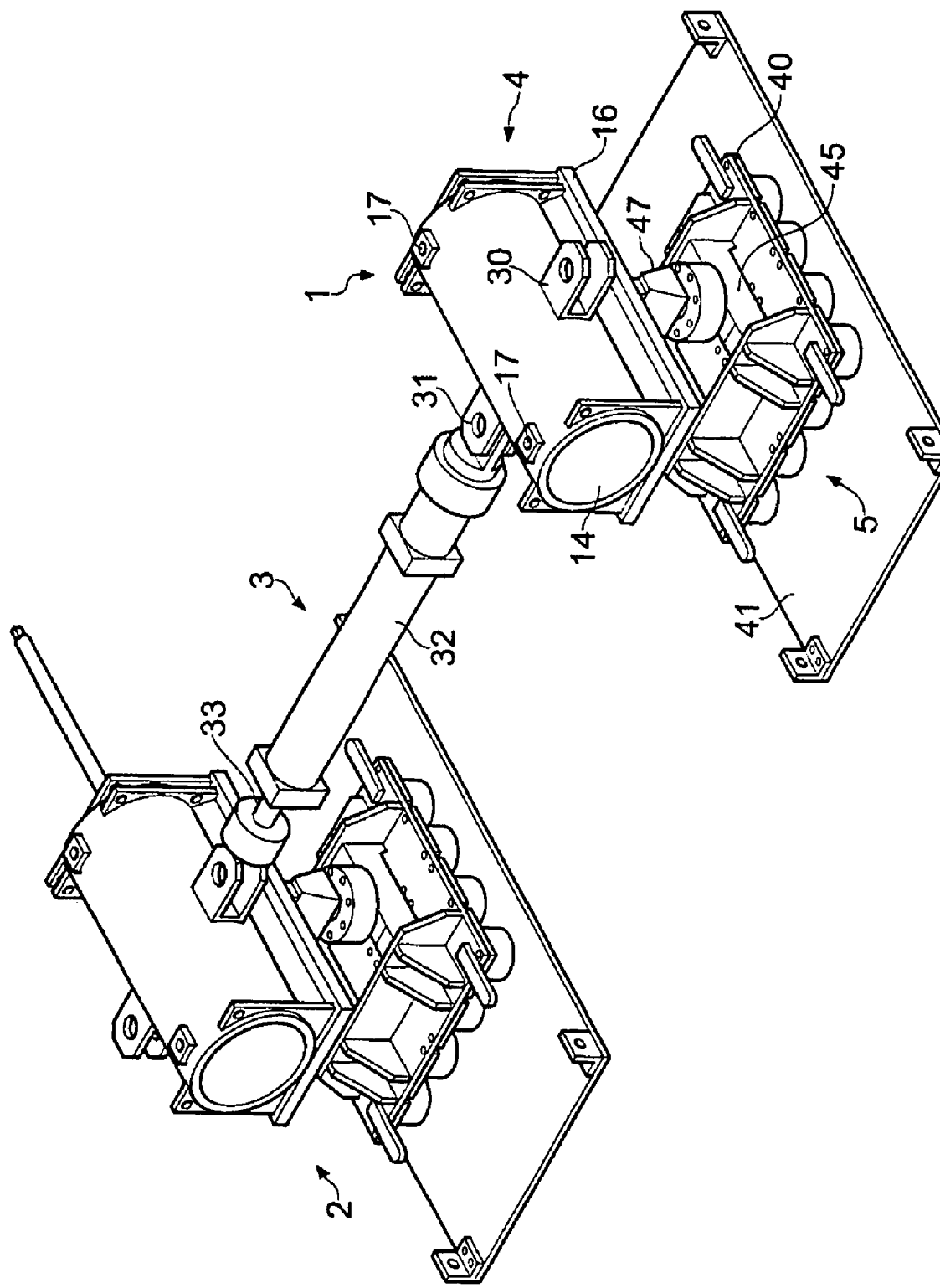
FIG. 1 is an isometric view of apparatus for applying bending load to an axle of an aircraft landing gear.

Apparatus for applying bending load to an axle of an aircraft landing gear is shown in FIG. 1. The apparatus comprises an aft unit 1 and a forward unit 2, connected by an X-load actuator 3. The aft unit 1 is coupled to a first axle of a multi-wheeled bogie aircraft landing gear, and the forward unit 2 is coupled to a second axle, forward of the first axle.

The units 1,2 are mirror images of each other, so only the aft unit 1 will be described in detail.

Figure 2:
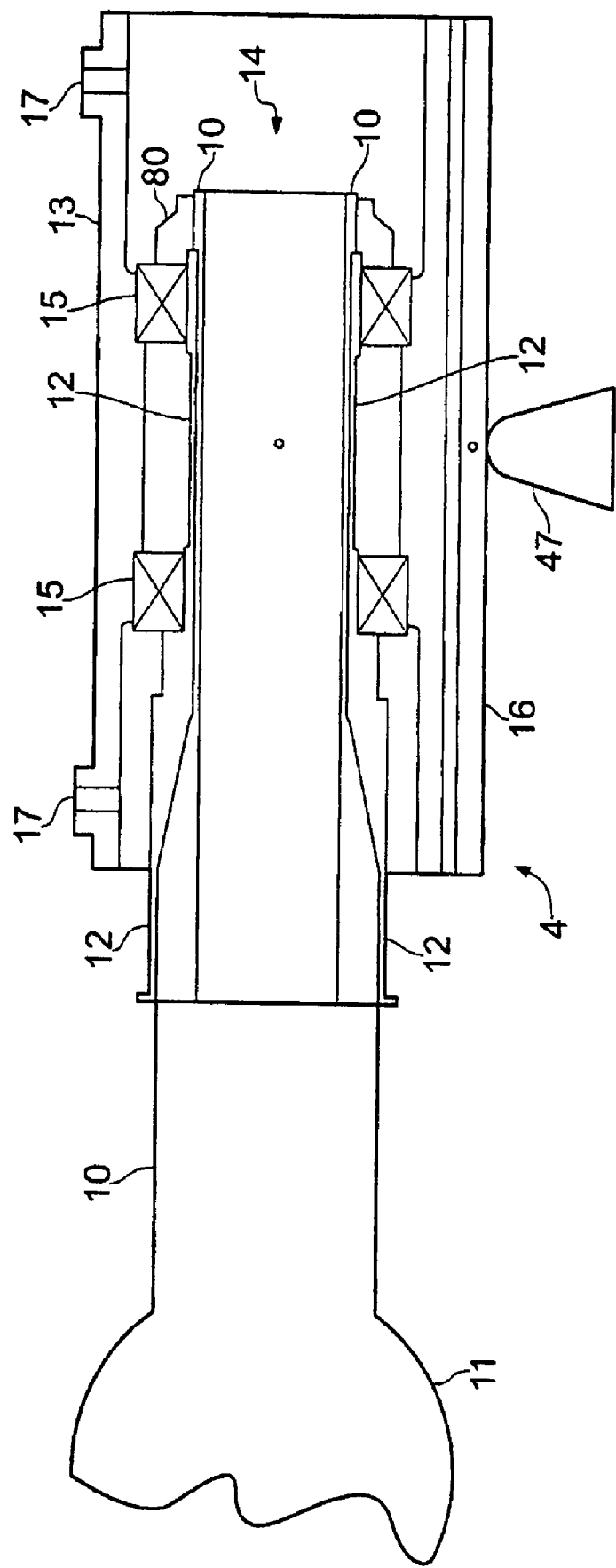
FIG. 2 is a cross-sectional view of the apparatus during a test phase.

The aft unit 1 comprises a dummy wheel 4, and a load tool 5. The dummy wheel 4 is shown in detail in FIGS. 2 and 3. FIG. 2 shows the dummy wheel 4 fitted to an axle 10. The axle 10 extends from a bogie beam 11 and an identical axle (not shown) extends from the other side of the bogie beam. The axle 10 has an axle sleeve 12 fitted onto its distal end.

The apparatus shown in FIG. 1 may be used to perform an on-aircraft test. In this case, the axle 10 and bogie beam 11 shown in FIG. 2 are part of a landing gear of the aircraft, and vertical load is applied to the axle by the weight of the aircraft. Alternatively the apparatus may be used to perform a laboratory test. In this case the vertical load is applied to the axle by a test system in the laboratory.

The dummy wheel is rated to support loads up to 30 tonnes (300 KN), and loads of up to 200 KN are typically applied during the testing process.

The dummy wheel 4 has a cylindrical body 13 with a bore 14 containing a pair of ring-shaped wheel bearings 15 which fit against the axle sleeve 12. A plate 16 with a generally planar lower surface is formed on the lower edge of the body 13. A pair of holes 17 in the upper edge of the body 13 can be used as lifting points. The distal end of the axle 10 protrudes from the end of the sleeve 12, and the dummy wheel is secured to the axle 10 by a wheel nut 80 shown in FIG. 2 which engages the axle 10.

Figure 3:
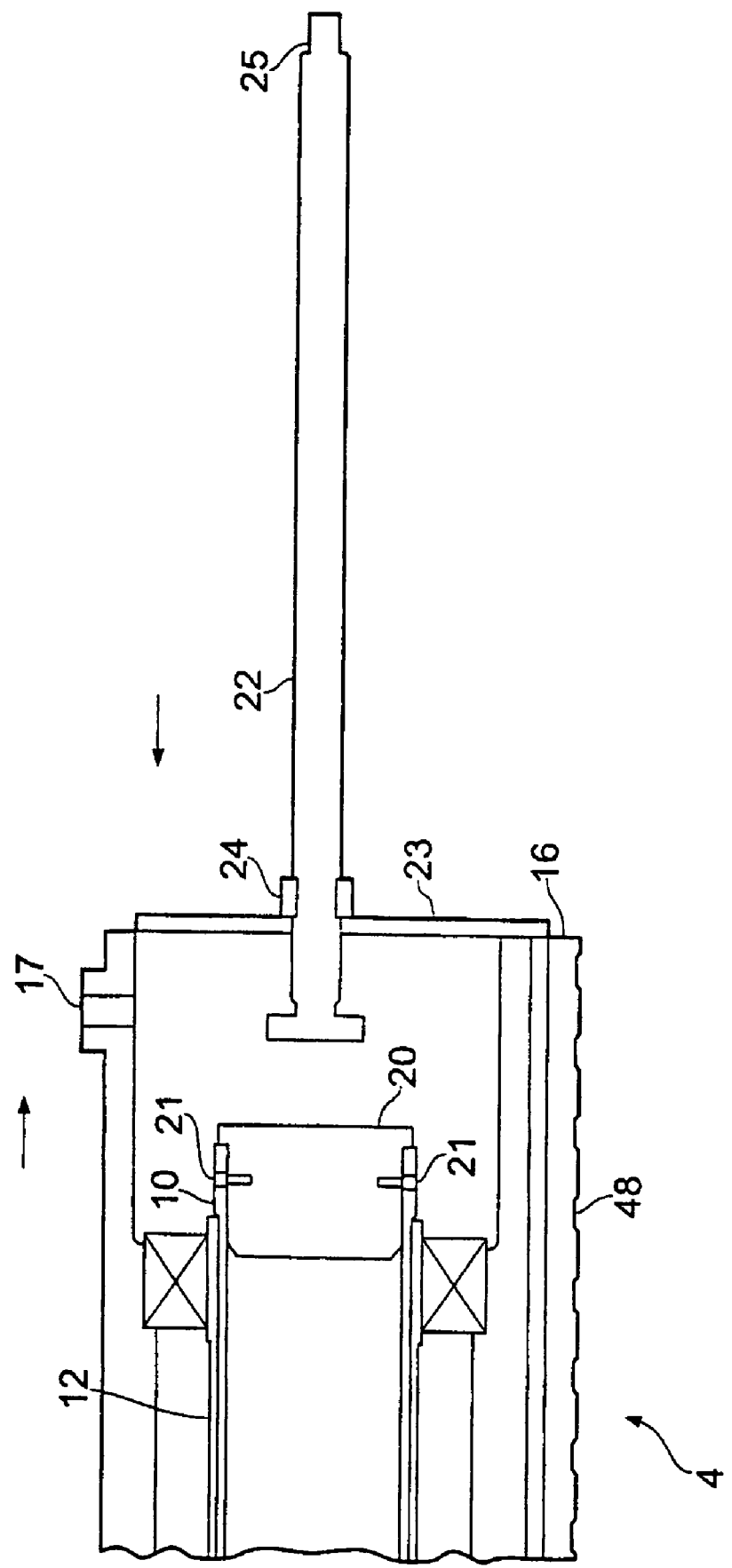
FIG. 3 is a cross-sectional view of the apparatus during an extraction phase.

The dummy wheel 4 is fitted onto the axle (and extracted from the axle) by a tool shown in FIG. 3. FIG. 3 shows the tool during the extraction phase. Before extraction, the wheel nut 80 is removed and a bung 20 is fitted inside the axle and fixed by a pair of locking nuts 21. The tool comprises a threaded rod 22 and a cover 23 with an internally threaded part 24. The cover 23 is fitted to the end of the dummy wheel as shown in FIG. 3 by four bolts (not shown). The rod 22 is fixed at its rear end 25, and as it is rotated it pulls the dummy wheel off the axle. The rod 22 is threaded in until its distal end engages the bung 20. At this point the dummy wheel has disengaged from the axle and can be removed. The reverse procedure is used to install the dummy wheel.

Figure 4:
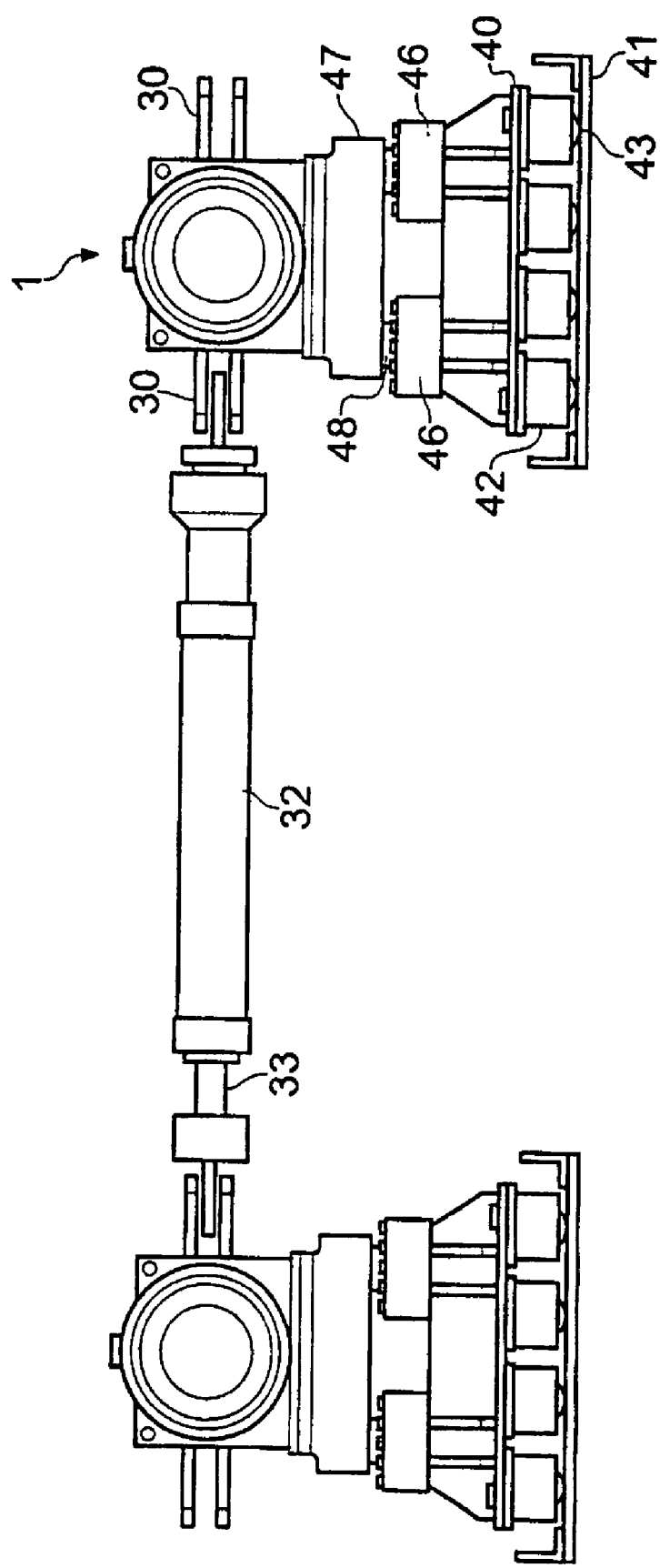
FIG. 4 is a side view of the apparatus.

As shown in FIGS. 1 and 4, the dummy wheel 4 has a U-shaped fitting 30 on both sides. The fitting has a pair of eyes 31 and is used to pivotally attach the X-load actuator 3 to the dummy wheel. The X-load actuator 3 comprises a hydraulic cylinder 32 which is attached to the aft dummy wheel 4, and a piston 33 which is attached to the other dummy wheel. The end of the cylinder 32 has an eye (not shown) which lines up with the eyes 31 and receives a pin (not shown).

The load tool 5 comprises a base 40 supported by a lifting platform 41. The base 40 can move freely in two dimensions over the platform 41 by means of a rolling-element bearing provided by an array of sixteen 2000 kg "Hevi-Load™ 3" ball transfer units 42. Each ball transfer unit 42 has a load ball 43 (shown in FIG. 4) which rotates on a bed of small balls supported on a hardened steel, precision machined table (not shown).

The base 40 carries a support structure comprising a pair of beams 45 and a pair of cylindrical pedestals 46 shown most clearly in FIG. 4. The pedestals 46 support a knife 47 via shim packs 48.

As shown in FIG. 2, the knife 47 has a tip with a convex outer surface which engages the lower surface of the plate 16 so as to apply a bending load to the axle via the dummy wheel bearings. The lower surface of the plate is generally planar but has a series of recesses 48 shown in FIG. 3. One of the recesses 48 is shown in detail in FIGS. 5 and 6. The recess 48 has a curved surface with a constant radius of curvature R. The recess 48 has a pair of parallel edges 49 which extend across the width of the plate 16, at right angles to the axis of the dummy wheel. The tip of the knife, when viewed in plan, is not circular but rather has an elongate shape and extends across the width of the plate so that it engages with the recess along its full length. The knife 47 is not shown in FIGS. 5 and 6, but the curvature of the surface at the tip of the knife is modelled in FIGS. 5 and 6 by a circle shown in dotted lines.

Figure 5:
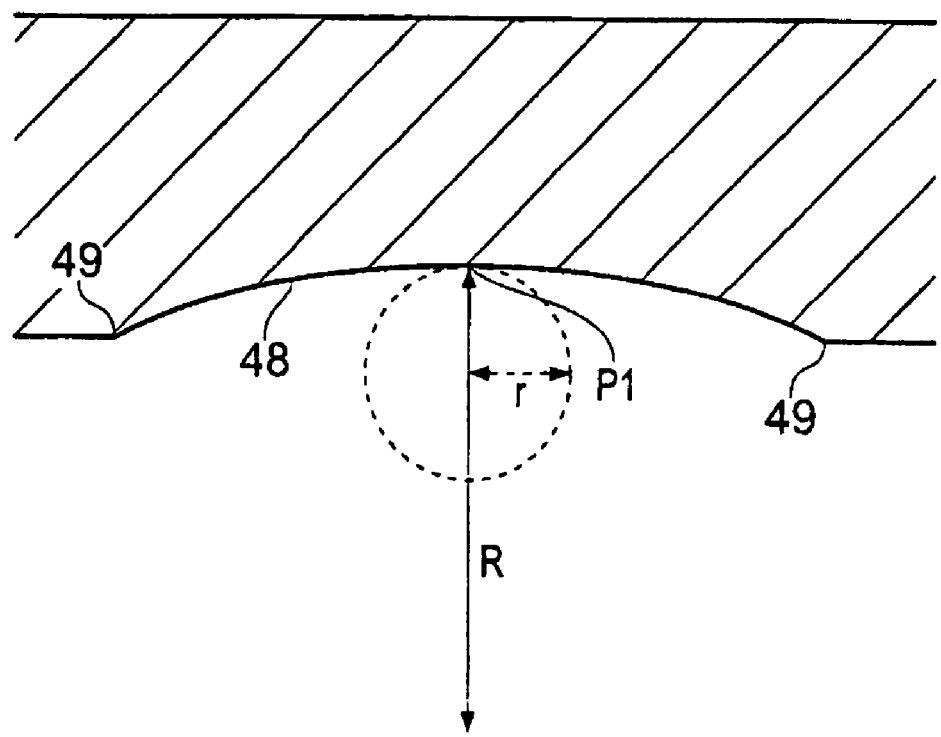
FIG. 5 is a schematic view showing the dummy wheel in an unloaded position.
Figure 6:
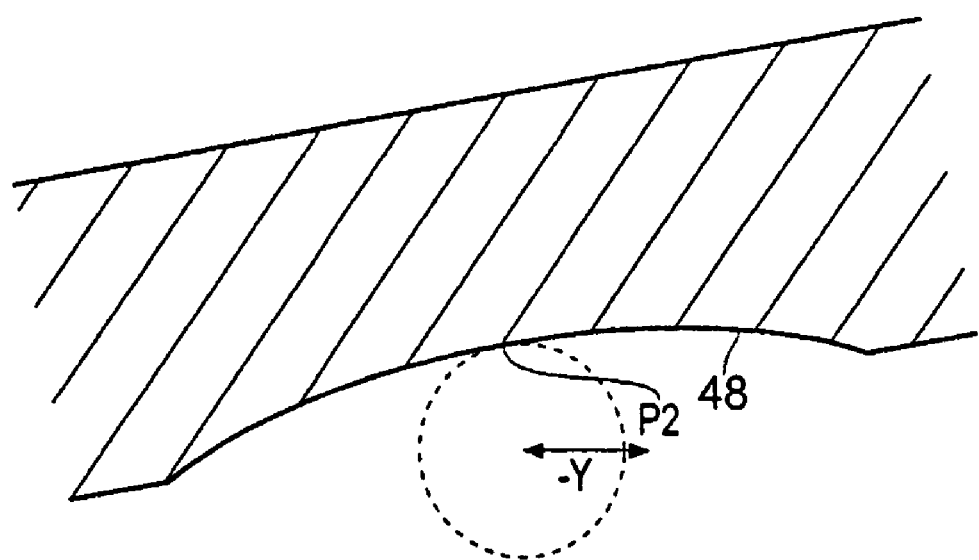
FIG. 6 is a schematic view showing the dummy wheel in a loaded position.

As shown in FIGS. 5 and 6, the radius of curvature R of the recess 48 is greater than the radius of curvature r of the tip of the knife. As a result, as the axle bends, the dummy wheel rolls over the tip of the knife between the unloaded position shown in FIG. 5 (in which the recess contacts the knife at a point P1 at the top of the knife tip) and the loaded position shown in FIG. 6 (in which the recess contacts the knife at a point P2 slightly below the highpoint P1). This rolling motion between the dummy wheel and the knife gives low frictional losses compared with a sliding arrangement. Low frictional losses enable a precisely known load to be applied to the dummy wheel. Also, the convex shape of knife tip results in a relatively small area of contact P1,P2 with the dummy wheel. This enables the knife to apply load to the dummy wheel at a precisely known position. The concave shape of the recess 48 ensures that the point of contact P1,P2 is positioned precisely at its centre.

The ratio R/r is exaggerated in FIGS. 5 and 6 for purposes of illustration. Typically the ratio between the two radii R/r is no greater than 3:1, and in a preferred case the radius r is 25 mm and the radius R is 50 mm (giving a ratio of 2:1). The load tool and dummy wheel are made of very hard steel to provide low hysteresis. The surfaces shown in FIGS. 5 and 6 have constant radii of curvature but other curve profiles may be employed such as parabolic curves.

In FIG. 2 the knife is engaging a recess which is aligned with the wheel centre, that is at a point half way between the dummy wheel bearings 15. As the axle bends, the dummy wheel exerts a slight inward force on the knife (that is, in the −Y direction to the left from the viewpoint of FIGS. 2, 5 and 6). As a result the knife moves left slightly due to the low friction bearing provided by the ball transfer units 42. The degree of translational movement (labelled −Y) is exaggerated in FIG. 6 for the purposes of illustration. This −Y translation relative to the lifting platform 41, in combination with the rolling motion between the knife and dummy wheel, enables the load tool to apply load to the dummy wheel with a moment arm (relative to the axle strain gauges) which does not vary (or only varies slightly) as the axle bends.

By expanding or contracting the X-load actuator 3, the two dummy wheels can be either forced apart or pulled together, causing the axles to bend horizontally in the X-direction. The units 1,2 move on their respective bearings in response to this horizontal bending.

The units 1,2 have strain gauges (not shown) for measuring the amount of vertical load being applied to the dummy wheels. Bending and shear of the axles is measured by strain gauges (not shown) mounted to the axles. By comparing the measured strain with the known applied bending loads, the performance of the landing gear can be measured. The construction of the units 1,2 enables a precisely known vertical load to be applied to the axle with a known moment arm relative to the strain gauges mounted to the axle.

Figure 7:
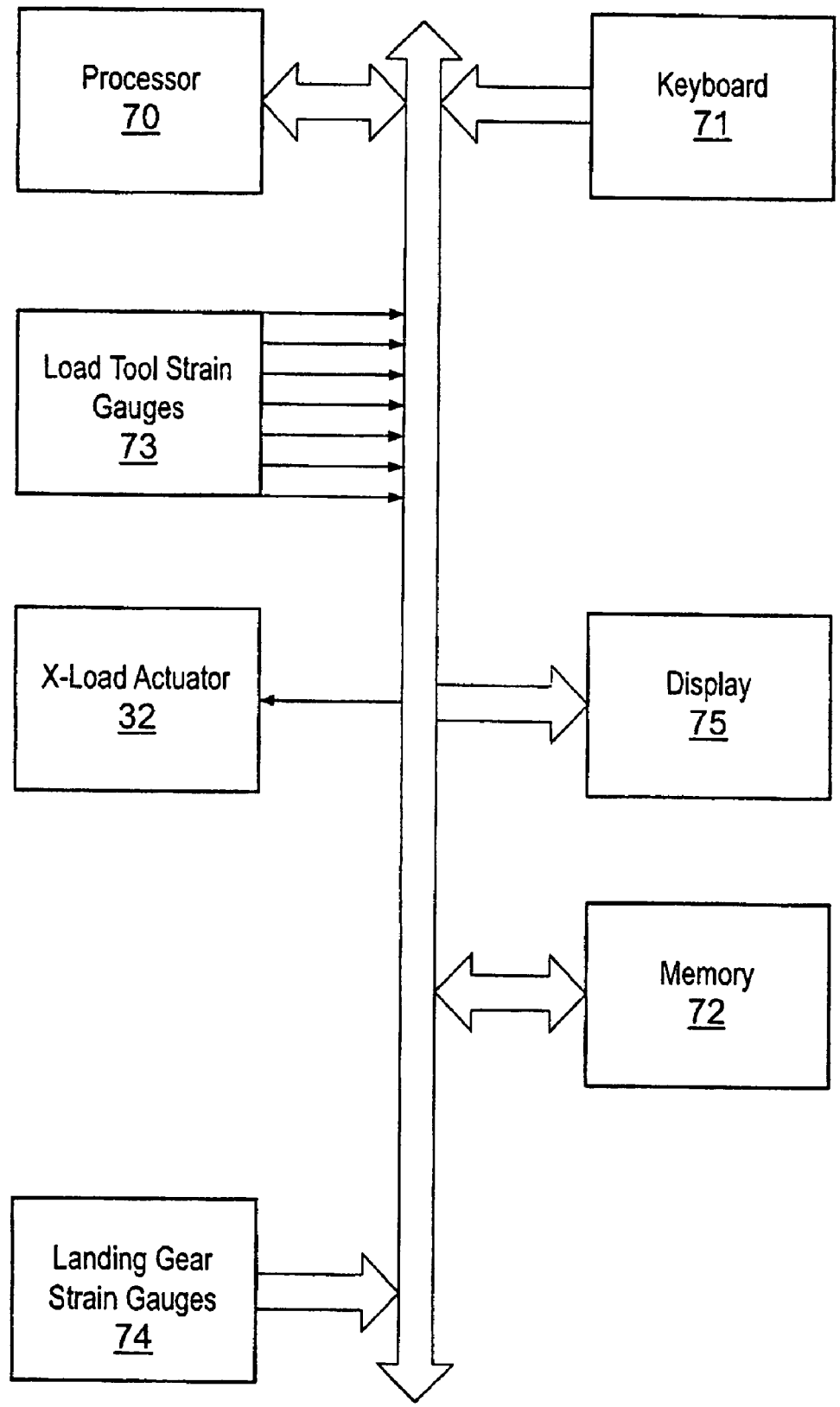
FIG. 7 is a schematic view of the electronic control system.

FIG. 7 is a schematic view of the electronic system of the fixture coupled with a flight test installation (FTI) system on the aircraft. Strain gauges 73 are mounted on the units 1,2 and the X-load actuator 32 in order to measure the load applied to the dummy wheels. Instead of using a strain gauge, the load applied by the X-load actuator 32 may alternatively be measured by measuring pressure in the hydraulic actuator. Similarly, the landing gear axle has a set of strain gauges indicated schematically at 74 in FIG. 7. The electronic system of the fixture is coupled to the FTI bus shown in FIG. 7, and a processor 70 onboard the aircraft. The readings from the strain gauges 73,74 are stored in a memory 72 onboard the aircraft during the loading sequence. The strain gauge readings can then be used by the processor 70 to calculate the coefficients of a transfer function linking the load applied with the load measured by the landing gear strain gauges 74, and to verify a mathematical model used to design the landing gear. Appropriate reports can be generated and output on a display 75. These reports form part of the aircraft certification requirements of the aircraft manufacturer.

Although the invention has been described above with reference to one or more preferred embodiments, it will be appreciated that various changes or modifications may be made without departing from the scope of the invention as defined in the appended claims.

The invention claimed is:

1. Apparatus for applying a bending load to an axle of an aircraft landing gear, the apparatus comprising:
   a dummy wheel having a dummy wheel bearing and an axis of rotation; and
   a load tool having a convex outer surface when viewed in cross section with the plane of said cross section parallel with said axis of rotation of said dummy wheel, said load tool configured to engage the dummy wheel and to apply the bending load to the axle via the dummy wheel bearing, wherein the dummy wheel is shaped to enable it to roll over the convex outer surface of the load tool as the axle bends.

2. The apparatus of claim 1 wherein the load tool has a load tool bearing which permits the load tool to move as it applies the bending load to the axle.

3. The apparatus of claim 2 wherein the load tool bearing is a linear load tool bearing which permits the load tool to move in a straight line as it applies the bending load to the axle.

4. The apparatus of claim 2 wherein the load tool bearing is a rolling-element bearing.

5. The apparatus of claim 2 wherein the load tool bearing permits the load tool to move in two orthogonal directions.

6. The apparatus of claim 1 further comprising an actuator for applying bending load to the axle in a different direction to the load tool.

7. The apparatus of claim 6 wherein the actuator is connected to the dummy wheel at one end and to another axle of the aircraft landing gear at another end.

8. A system for testing an axle of an aircraft landing gear, the system comprising:
   the apparatus of claim 1 for applying bending load to the axle;
   one or more sensors for sensing the load applied to the axle; and
   one or more sensors for sensing the response of the axle to the applied load.

9. Apparatus for applying bending load to an axle of an aircraft landing gear, the apparatus comprising a dummy wheel having a dummy wheel bearing; and a load tool having a convex outer surface which is configured to engage the dummy wheel when in use so as to apply the bending load to the axle via the dummy wheel bearing, wherein the dummy wheel is shaped to enable it to roll over the convex outer surface of the load tool as the axle bends, wherein the dummy wheel has a series of recesses formed in its surface, the recesses being shaped to enable them to roll over the convex outer surface of the load tool.

10. The apparatus of claim 9 wherein each recess has a curved concave surface.

11. The apparatus of claim 9 wherein each recess is elongate in shape when viewed in plan.

12. Apparatus for applying a bending load to an axle of an aircraft landing gear, the apparatus comprising a dummy wheel having a dummy wheel bearing; and a load tool having a convex outer surface which is configured to engage the dummy wheel when in use so as to apply the bending load to the axle via the dummy wheel bearing, wherein the dummy wheel is shaped to enable it to roll over the convex outer surface of the load tool as the axle bends, wherein the convex outer surface of the load tool is elongate in shape when viewed in plan.

13. A method of applying a bending load to an axle of an aircraft landing gear, the method comprising:
   fitting a dummy wheel to the axle via a dummy wheel bearing and having an axis of rotation; and
   applying the bending load to the axle by engaging the dummy wheel with an outer surface of a load tool, said outer surface having a convex shape when viewed in cross section where the plane of the cross section is parallel with said axis of rotation, wherein the bending of the axle causes the dummy wheel to roll over the convex outer surface of the load tool.

14. The method of claim 13 wherein the bending of the axle causes the load tool to move.

15. The method of claim 14 wherein the bending of the axle causes the load tool to move in a straight line.

16. The method of claim 13 wherein the bending load is applied to the axle in a first direction by the load tool, and the method further comprises applying bending load to the axle in a second direction.

17. The method of claim 16 wherein the bending load in the second direction is applied by an actuator which is connected to the dummy wheel at one end and to another axle of the aircraft landing gear at another end.

18. The method of claim 13 wherein the load tool applies the bending load to the axle in a vertical direction.

19. A method of testing an axle of an aircraft landing gear, the method comprising:
   applying a bending load to the axle by the method of claim 13;
   sensing the load applied to the axle; and
   sensing the response of the axle to the applied load.

20. Apparatus for applying a bending load to an axle of an aircraft landing gear, the apparatus comprising:
   a dummy wheel having a dummy wheel bearing; and
   a load tool having a convex outer surface which is configured to engage the dummy wheel and to apply the bending load to the axle via the dummy wheel bearing, wherein the dummy wheel is shaped to enable it to roll over the convex outer surface of the load tool as the axle bends, wherein the load tool bearing permits the load tool to move in two orthogonal directions, wherein the load tool has a load tool bearing which permits the load tool to move as it applies the bending load to the axle.

21. A method of applying a bending load to an axle of an aircraft landing gear, the method comprising:
   fitting a dummy wheel to the axle via a dummy wheel bearing;
   applying a bending load in a first direction to the axle by engaging the dummy wheel with a convex outer surface of a load tool, wherein the bending of the axle causes the dummy wheel to roll over the convex outer surface of the load tool; and
   applying a bending load to the axle in a second direction, wherein the bending load in the second direction is applied by an actuator which is connected to the dummy wheel at one end and to another axle of the aircraft landing gear at another end.

* * * * *